United States Patent
Baltekin et al.

(10) Patent No.: US 11,946,029 B2
(45) Date of Patent: Apr. 2, 2024

(54) MICROFLUIDIC DEVICE

(71) Applicant: ASTREGO DIAGNOSTICS AB, Uppsala (SE)

(72) Inventors: Özden Baltekin, Uppsala (SE); Ove Öhman, Uppsala (SE); Martin Lovmar, Mölndal (SE); Johan Elf, Uppsala (SE); Mikael Olsson, Uppsala (SE)

(73) Assignee: ASTREGO DIAGNOSTICS AB, Uppsala (SE)

( * ) Notice: Subject to any disclaimer, the term of this patent is extended or adjusted under 35 U.S.C. 154(b) by 830 days.

(21) Appl. No.: 16/969,881

(22) PCT Filed: Feb. 15, 2019

(86) PCT No.: PCT/SE2019/050134
§ 371 (c)(1),
(2) Date: Aug. 13, 2020

(87) PCT Pub. No.: WO2019/160491
PCT Pub. Date: Aug. 22, 2019

(65) Prior Publication Data
US 2020/0407671 A1   Dec. 31, 2020

(30) Foreign Application Priority Data
Feb. 16, 2018 (SE) .................... 1850168-4

(51) Int. Cl.
*C12M 1/26* (2006.01)
*B01D 61/18* (2006.01)
(Continued)

(52) U.S. Cl.
CPC ............. *C12M 23/16* (2013.01); *B01D 61/18* (2013.01); *B01D 63/005* (2013.01);
(Continued)

(58) Field of Classification Search
None
See application file for complete search history.

(56) References Cited

U.S. PATENT DOCUMENTS

| 5,922,210 A | 7/1999 | Brody et al. |
| 10,570,437 B2 | 2/2020 | Elf et al. |

(Continued)

FOREIGN PATENT DOCUMENTS

| CN | 101107549 A | 1/2008 |
| CN | 106471122 A | 3/2017 |

(Continued)

OTHER PUBLICATIONS

Baltekin, Özden et al., Antibiotic susceptibility testing in less than 30 min using direct single-cell imaging, PNAS, vol. 114, No. 34, pp. 9170-9175 (Aug. 22, 2017).

(Continued)

*Primary Examiner* — Brian R Gordon
(74) *Attorney, Agent, or Firm* — Porter Wright Morris & Arthur LLP (57) ABSTRACT

A microfluidic device (1) comprises a substrate (10) having a flow input channel (30) in fluid connection with a first fluid port (31) and a flow output channel (40) in fluid connection with a third fluid port (41) and cell channels (20) disposed between the flow input channel (30) and the flow output channel (40). The cell channels (20) comprise a respective obstruction (25) designed to prevent the target cells from passing the respective obstruction (25) and into the flow output channel (40). The microfluidic device (1) also comprises a pre-filter (50) with a filter channel (60) in fluid connection with a first filter port (61) and pre-filter channels (70) adapted to accommodate the target cells. A respective first end (72) of the pre-filter channels (70) is in fluid connection with the filter channel (60) and a respective (Continued)

second end (74) of the pre-filter channels (70) is in fluid connection with the flow input channel (30).

12 Claims, 8 Drawing Sheets

(51) Int. Cl.
    *B01D 63/00*     (2006.01)
    *B01L 3/00*     (2006.01)
    *C12M 3/06*     (2006.01)

(52) U.S. Cl.
    CPC ... *B01L 3/502746* (2013.01); *B01L 3/502761* (2013.01); *C12M 33/14* (2013.01); *B01L 2300/0681* (2013.01)

(56) References Cited

U.S. PATENT DOCUMENTS

| | | | |
|---|---|---|---|
| 2008/0118207 A1 | 5/2008 | Yamamoto et al. | |
| 2012/0258459 A1* | 10/2012 | Huang | B01L 3/50255 210/767 |
| 2013/0157283 A1* | 6/2013 | Yung | G01N 33/54333 435/7.1 |
| 2013/0337500 A1 | 12/2013 | Tan et al. | |
| 2014/0087456 A1 | 3/2014 | Lim et al. | |
| 2014/0128285 A1* | 5/2014 | Rowat | G01N 29/222 506/10 |
| 2014/0227777 A1* | 8/2014 | Choi | G01N 1/34 435/309.1 |
| 2014/0228250 A1* | 8/2014 | Wang | C12Q 1/00 506/14 |
| 2016/0025761 A1* | 1/2016 | West | G01N 33/56961 435/395 |
| 2016/0333295 A1* | 11/2016 | Baker | C12M 23/16 |
| 2016/0340631 A1* | 11/2016 | Wang | C12N 5/0693 |
| 2017/0122937 A1* | 5/2017 | Arai | B01L 3/502761 |
| 2019/0161715 A1* | 5/2019 | Wang | B01L 3/502761 |
| 2020/0011775 A1* | 1/2020 | Alexander | B01L 3/502761 |
| 2020/0238288 A1* | 7/2020 | Lee | H05H 3/02 |

FOREIGN PATENT DOCUMENTS

| | | |
|---|---|---|
| WO | 2006/079007 A2 | 7/2006 |
| WO | 2016/007063 A1 | 1/2016 |
| WO | 2016/007068 A1 | 1/2016 |
| WO | 2017/188962 A1 | 11/2017 |

OTHER PUBLICATIONS

Wang, Ping et al., Robust Growth of *Escherichia coli*, Current Biology, vol. 20, pp. 1099-1103 (Jun. 22, 2010).

Office Action from corresponding Japanese Application No. 2020-541502 dated Feb. 28, 2023, with English Translation.

Baltekin, Özden et al., Supporting Information for 10.1073/pnas.1708558114, Antibiotic susceptibility testing in less than 30 minus-ing direct single-cell imaging, PNAS, vol. 114, No. 34, pp. 1-8 (Aug. 22, 2017).

* cited by examiner

MICROFLUIDIC DEVICE

TECHNICAL FIELD

The present invention is generally directed to a microfluidic device, and in particular to such a microfluidic device that can be used for analysis of biological samples comprising contaminating particles and target cells.

BACKGROUND

The recent development in single cell biology has made it clear that isogenic cells can display large differences in gene expression and behavior also when grown under identical conditions. New devices are thereby needed to characterize cell-to-cell differences in phenotypes over time. Such devices need to meet certain criteria in order to be an effective tool in culturing and monitoring single cells. For instance, these devices should be easy to load with cells so that one can monitor phenotypic characteristics immediately after loading. Furthermore, many different individual cells need to be grown in parallel to characterize the cell-to-cell differences and to overcome measurement errors in the characterization of individual cells by averaging. The devices should be designed to enable culturing of cells for a long period of time under constant and well-controlled growth conditions to monitor, for example, lineage dependent dynamics. It is further preferred if the devices enable change of culturing conditions to monitor dynamic changes in response to new culture media or test agents. For instance, it could be advantageous to test different culture media on isogenic cells in parallel or monitor the response to media changes on different cell strains in parallel.

A desired application of microfluidic devices is to rapidly and in parallel monitor the phenotypic response of target cells, such as bacteria, in a biological sample to a set of antibiotics or other test agents immediately after the target cells have been loaded in the microfluidic device. In such an application, it would be advantageous to be able to directly load the microfluidic device with the biological sample to gain speed in the analysis.

A prior art microfluidic device, denoted the "Mother Machine", is disclosed in Wang et al., *Current Biology* 2010, 20: 1099-1103. The Mother Machine allows for monitoring cells in many different cell channels in parallel. However, this prior art microfluidic device has several shortcomings. For instance, cell loading is complicated and it is hard to rapidly change culture conditions in the microfluidic device.

Further microfluidic devices that are useful for analysis of biological samples are shown in WO 2016/007063 and WO 2016/007068.

Baltekin et al., *PNAS* 2017, 114(34): 9170-9175 discloses a fast antibiotic susceptible testing (AST) test, FASTest, using a microfluidic device. A filter region with different zones of gradually decreasing filtration size is provided in the ports of the microfluidic device to capture dust, large precipitates in the growth medium and air bubbles.

There is a need for a microfluidic device that can be used for biological samples comprising contaminating particles that otherwise may prevent capture of target cells in the microfluidic device.

SUMMARY

It is a general objective to provide a microfluidic device that can be loaded with a biological sample comprising contaminating particles.

This and other objectives are met by embodiments as disclosed herein.

An aspect of the embodiments relates to a microfluidic device comprising a substrate having cell channels adapted to accommodate target cells. The microfluidic device also comprises a flow input channel having a first end in fluid connection with a first fluid port and a flow output channel in fluid connection with a third fluid port. A respective first end of the cell channels is in fluid connection with the flow input channel and a respective second end of the cell channels is in fluid connection with the flow output channel. The cell channels comprise a respective obstruction designed to prevent the target cells from passing the respective obstruction and into the flow output channel. The microfluidic device further comprises a pre-filter comprising a filter channel having a first end in fluid connection with a first filter port and pre-filter channels adapted to accommodate the target cells. A respective first end of the pre-filter channels is in fluid connection with the filter channel and a respective second end of the pre-filter channels is in fluid connection with the flow input channel.

Another aspect of the embodiments relates to a method of operating a microfluidic device according to the embodiments. The method comprises inducing a fluid flow from the flow input channel through the pre-filter channels and into the filter channel.

The microfluidic device comprises a pre-filter designed to capture and/or exclude contaminating particles present in a biological sample in addition to the target cells, or at least significantly reduce the risk of such contaminating particles from entering the cell channels. The pre-filter can be cleaned from clogging contaminating particles that otherwise would obstruct the flow of the biological sample through the pre-filter and the cell channels. The microfluidic device can thereby be used for biological samples comprising a high concentration of contaminating particles and/or a low ratio of target cells relative to the contaminating particles.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present invention is generally directed to a microfluidic device, and in particular to such a microfluidic device that can be used for analysis of biological samples comprising contaminating particles and target cells.

Microfluidic devices have been proposed to analyze and monitor target cells present in a biological sample to determine various characteristics of the target cells, such as phenotypic and/or genotypic characteristics and traits. This approach generally works well in the case of substantially pure biological samples mainly comprising the target cells in a liquid medium, or if the biological sample comprises the target cells at a comparatively high concentration.

However, in several applications the biological sample can be complex, additionally comprising so-called contaminating particles and/or comprising the target cells at a comparatively low concentration. The contaminating particles could include cells other than the target cells, cell debris and non-cell material, such as dust and/or dirt particles. In these applications, the contaminating particles may clog the microfluidic device thereby preventing efficient capture of the target cells present in the biological sample in the microfluidic device. Furthermore, if the biological sample comprises comparatively higher concentrations of the contaminating particles as compared to the target cells, the contaminating particles may outcompete the target cells during the capture in the microfluidic device with the consequence of not capturing any or too few target cells in the microfluidic device. In either case, there will not be sufficient number of target cells captured in the microfluidic device in order to make an efficient analysis of the target cells and determine characteristics thereof.

A typical situation would be having a blood sample taken from a (tentative) sepsis patient. In such a case, the blood sample most often comprises comparatively low concentrations of infection-causing bacteria as target cells and comparatively much higher concentrations of white blood cells (WBCs) and red blood cells (RBCs) as contaminating particles.

This means that if such a blood sample is loaded into a microfluidic device, the WBCs and RBCs may obstruct and clog cell channels in the microfluidic device and/or occupy substantially all cell channels, in which the bacteria should be captured. As a consequence, no or far too few bacteria will be captured in the microfluidic device with such a blood sample.

A microfluidic device with a filter has been proposed in Baltekin et al., *PNAS* 2017, 114(34): 9170-9175. The microfluidic device then includes a filter region in the input ports. This filter region may be efficient to capture dust and large precipitates in the input medium and remove air bubbles from the medium. However, a biological sample with a lot of contaminating particles at a size similar to the target cells, such as a blood sample, would eventually clog the filter region thereby preventing any flow of blood through the port and further into the microfluidic device.

There is, thus, a need for a microfluidic device that can be used for analysis of biological samples comprising contaminating particles, such as a blood sample with WBCs and RBCs.

The microfluidic device of the present embodiments comprises a pre-filter that is designed to remove at least a portion of the contaminating particles, thereby preventing or at least significantly reducing the number of such contaminating particles that may reach the cell channels used to capture target cells in the microfluidic device. A significant advantage of the microfluidic device and the pre-filter of the embodiments is that the pre-filter can be cleaned if it would be clogged or obstructed by contaminating particles. Such a cleaning of the pre-filter can take place during operation of the microfluidic device and even if target cells have already been captured in cell channels.

Thus, even if the biological sample comprises comparatively a lot of such contaminating particles that may clog the pre-filter and the microfluidic device, the pre-filter can be cleaned to remove such clogging contaminating particles to thereby continue capturing target cells from the biological sample in the microfluidic device.

Figure 1:
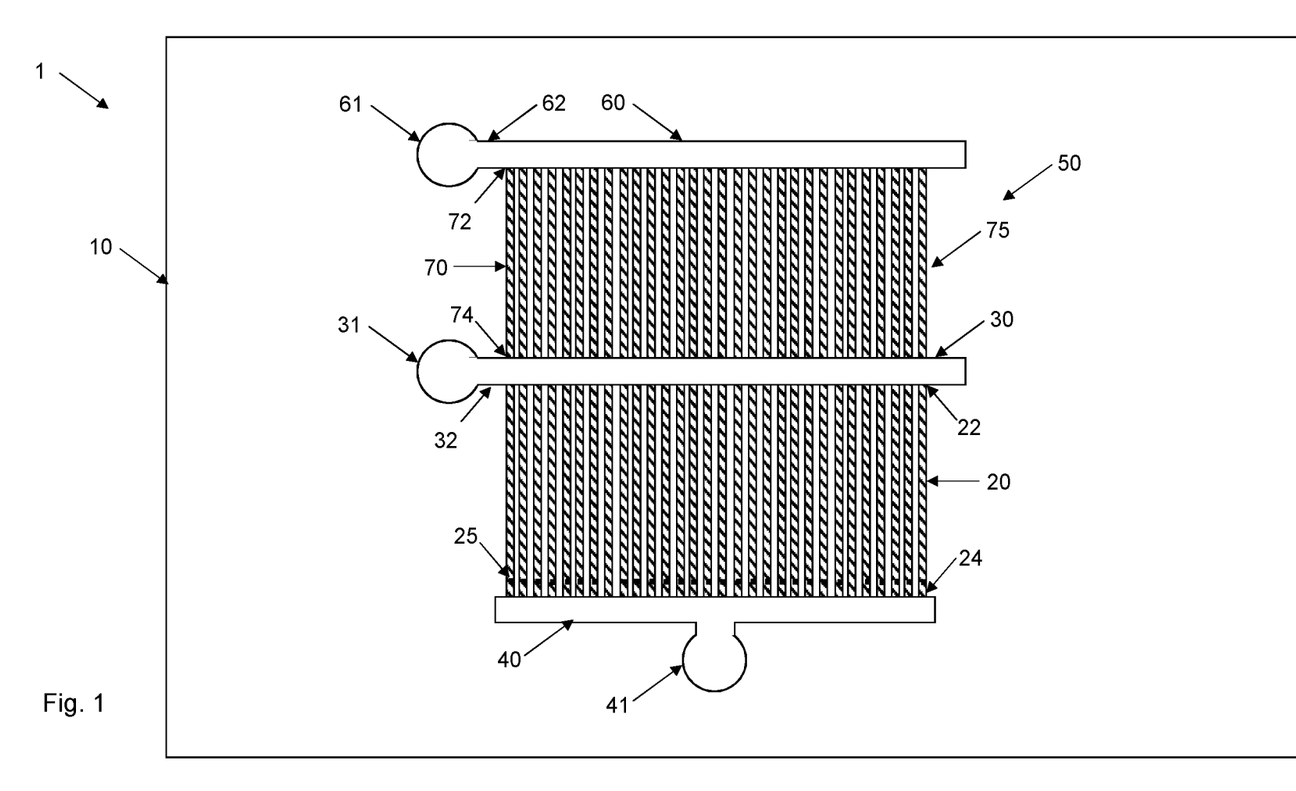
FIG. 1 is an illustration of a microfluidic device according to an embodiment.

FIG. 1 is an illustration of a microfluidic device 1 according to an embodiment. The microfluidic device 1 comprises a substrate 10 having cell channels 20, also referred to as cell traps, adapted to accommodate target cells. The microfluidic device 1 also comprises a flow input channel 30 having a first end 32 in fluid connection with a first fluid port 31. A respective first end 22 of the cell channels 20 is in fluid connection with the flow input channel 30. The microfluidic device 1 further comprises a flow output channel 40 in fluid connection with a third fluid port 41. A respective second end 24 of the cell channels 20 is in fluid connection with the flow output channel 40. The cell channels 20 comprise a respective obstruction 25 designed to prevent or at least restrict the target cells from passing the respective obstruction 25 and into the flow output channel 40. The microfluidic device 1 additionally comprises a pre-filter 50. The pre-filter 50 comprises a filter channel 60 having a first end 62 in fluid connection with a first filter port 61. The pre-filter 50 also comprises pre-filter channels 70 adapted to accommodate the target cells. A respective first end 72 of the pre-filter channels 70 is in fluid connection with the filter channel 60 and a respective second end 74 of the pre-filter channels 70 is in fluid connection with the flow input channel 30.

The substrate 10 of the microfluidic device 1 has multiple, i.e., at least two but most generally several tens of, several hundred or even several thousand or several hundred thousand, cell channels 20 extending between the flow input channel 30 and the flow output channel 40. The cell channels 20 are preferably parallel with each other as shown in FIG. 1 with the first ends 22 in fluid connection with the flow input channel 30 and the opposite second ends 24 in fluid connection with the flow output channel 40. Accordingly, a biological sample present in the flow input channel 30 may flow through the cell channels 20 and further into the flow output channel 40 and out through the third port 41.

The cell channels 20 are dimensioned, i.e., having a size, such as width and height or diameter, and shape, that is sufficiently large to allow target cells present in the biological sample in the flow input channel 30 to enter the cell channels 20. Any contaminating particles having passed through the pre-filter 50 and having a size and/or shape that is too big or not adapted to the cross-sectional size and shape of the cell channels 20 will not enter the cell channels 20 through the first ends 22.

In particular embodiments, the dimension of the cell channels 20 is in the range of 100 nm to 100 μm. The obstruction 25 of the cell channels 20 is designed to have a shape and dimension, such as diameter, width and/or height, that prevent the target cells from passing the obstruction 25 and enter the flow output channel 40. Accordingly, the target cells will become trapped and captured in the cell channels 20.

The obstruction 25 of a cell channel 20 is preferably arranged at or in connection with the second end 24 of the cell channel 20 as shown in FIG. 1. This allows capture of more than one target cell per cell channel 20 and/or growth, i.e., division, of the target cells inside the cell channel 20.

In order to prevent or at least significantly reduce the risk of contaminating particles blocking the entrances, i.e., the first ends 22, of the cell channels 20 and thereby blocking any target cells in the biological sample from entering the cell channels 20 and become captured therein, the pre-filter 50 is arranged upstream of the cell channels 20. This means that the pre-filter 50 will effectively remove at least a significant portion of any contaminating particles present in the biological sample and thereby prevent or reduce the number of such contaminating particles from reaching the flow input channel 30 and the cell channels 20.

In the embodiment of the pre-filter 50 shown in FIG. 1, the pre-filter 50 comprises multiple pre-filter channels 70 that are preferably parallel to each other. These pre-filter channels 70 may, in an embodiment, be substantially similar to the cell channels 20 but with the exception of not having any obstruction 25 as the cell channels 20 have.

The pre-filter channels 70 may then have a same cross-sectional size and shape as the cell channel 20 or may have a different such cross-sectional size and/or shape as long as the target cells can enter and flow through the pre-filter channels 70.

The pre-filter channels 70 may have a substantially uniform cross-sectional size and shape when traveling from the first end 72 at the filter channel 60 towards the second end 74 at the flow input channel 30. In another embodiment, the cross-sectional size and/or shape may change, either continuously or in one or more steps, from the first end 72 to the second end 74. For instance, the diameter, width or height of the pre-filter channels 70 could be larger at the first end 72 as compared to the second end 74. This narrowing of the pre-filter channels 70 could be continuous, i.e., smoothly decreasing diameter, width or height when going from the first end 72 to the second end 74. Alternatively, the narrowing of the pre-filter channels 70 could be step-wise in one or more steps.

Figure 7:
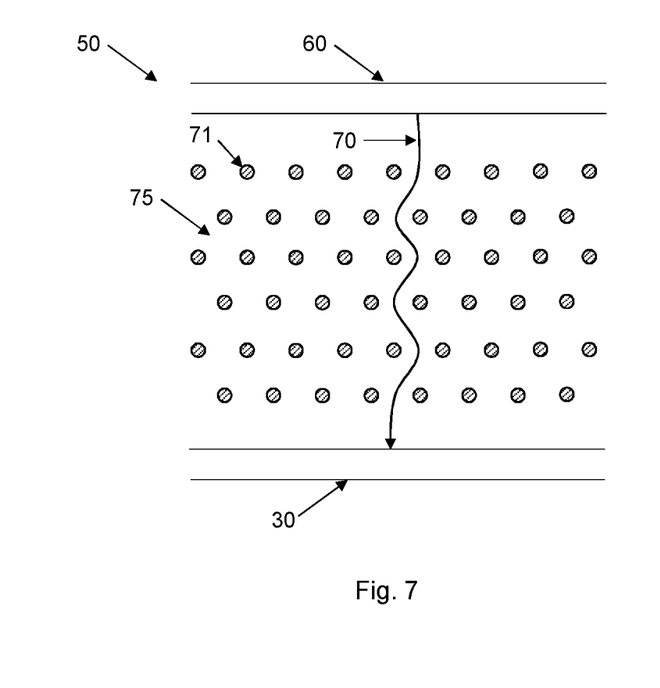
FIG. 7 schematically illustrates an embodiment of a pre-filter.
Figure 8:
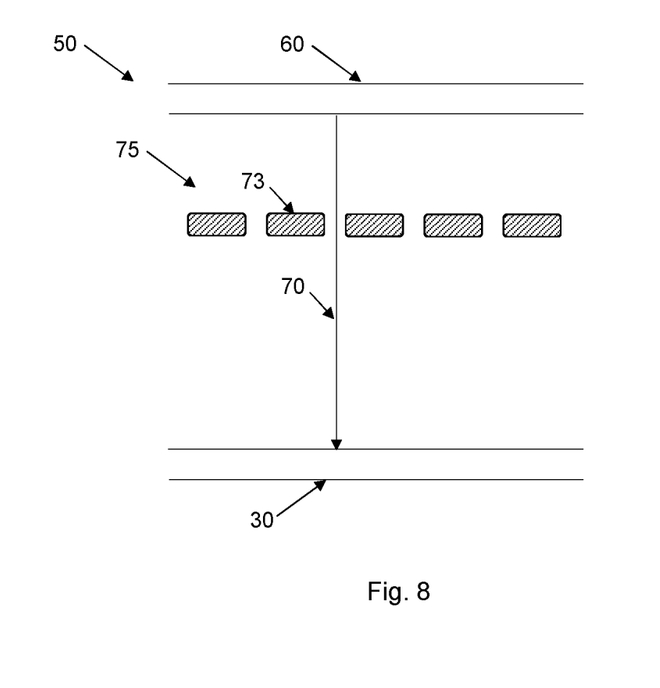
FIG. 8 schematically illustrates another embodiment of a pre-filter.

The embodiment of having parallel pre-filter channels 70 interposed between substrate material should merely be seen as an illustrative example of a pre-filter 50. FIGS. 7 and 8 illustrate other embodiments of a pre-filter 50 with pre-filter channels 70. In FIG. 7, multiple pillars 71 are arranged in the pre-filter 50 between the filter channel 60 and the flow input channel 30. These multiple pillars 71 form pre-filter channels 70 extending between the pillars 71 and from the filter channel 60 to the flow input channel 30. In an embodiment, the pillars 71 are uniformly distributed in a so-called pre-filter area or zone 75 between the filter channel 60 and the flow input channel 30. In such an embodiment, the inter-pillar distance between adjacent pillars 71 is substantially the same throughout the pre-filter area or zone 75. In an alternative embodiment, the pillars 71 may be more or less randomly distributed over the pre-filter area or zone 75 as long as there are pre-filter channels 70 extending between the filter channel 60 and the input channel 30 and having dimension sufficient to allow target cells to flow from the filter channel 60 through the pre-filter area or zone 75 and into the flow input channel 30.

In a further embodiment, the inter-pillar distance may change over the pre-filter area or zone 75, either continuously or step-wise, when going from the filter channel 60 to the flow input channel 30. For instance, the inter-pillar distance could be smaller between adjacent pillars 71 close to the flow input channel 30 as compared to between adjacent pillars 71 close to the filter channel 60.

FIG. 8 illustrates another embodiment of the pre-filter 50. In this embodiment, the pre-filter area or zone 75 comprises a row or array of filter structures 73 having openings in between. These openings thereby allow the target cells to pass through the row or array of filter structures 73. Thus, the pre-filter area or zone 75 comprises pre-filter channels 70 as indicated in the figure.

In FIG. 8, a single row or array of filter structures 73 is arranged in the pre-filter area or zone 75. This should merely be seen as an illustrative example. It is in fact possible to have multiple such rows or arrays arranged one after another to basically form a matrix of filter structures 73. In such a case, the filter structures 73 in different rows may be aligned to each other or may be at least partly displaced relative to each other. In the former case, the pre-filter channels 70 would be straight channels between the openings in the filter structures 73, whereas in the latter case the pre-filter channels 70 would zig-zag between displaced openings in different rows of filter structures 73.

In the case of multiple rows or arrays of filter structures 73, the distances between adjacent filter structures 73 could be the same in all rows or arrays, i.e., having uniformed openings. Alternatively, the distances between adjacent filter structures 73 could differ between different rows, such as having larger such distances and thereby openings for a row of filter structures 73 close to the filter channel 60 as compared to the distances and thereby openings for a row of filter structures 73 close to the flow input channel 30.

There are further alternative ways of forming pre-filter channels 70 in a pre-filter area or zone 75 than having parallel pre-filter channels 70 as in FIG. 1, pillar-defining pre-filter channels 70 as in FIG. 7 and pre-filter channels 70 between filter structures 73 as in FIG. 8. The embodiments are thereby not limited to these illustrative examples. For instance, continuous pores extending through the substrate or a semi-permeable membrane structure arranged in the pre-filter area or zone 75 between the filter channel 60 and the flow input channel 30 could alternative be used as pre-filter channels 70.

In the following, various embodiments of the microfluidic device 1 will be described in more detail and with a pre-filter 50 having a pre-filter area or zone 75 according to FIG. 1. However, these various embodiments of the microfluidic device 1 may alternatively have other pre-filter embodiments, such as the one in FIG. 7 or FIG. 8.

In operation of the microfluidic device 1 as shown in FIG. 1, a biological sample is preferably loaded into the microfluidic device 1 through the first filter port 61. The biological sample will flow through the filter channel 60 and into the pre-filter channels 70. Contaminating particles present in the biological sample and having a sufficiently large size, shape and/or rigidity are prevented from entering the first ends 72 of the pre-filter channels 70 and thereby remain in the filter channel 60. However, any target cells present in the biological sample will enter the first ends 72 and flow through the pre-filter channels 70 into the flow input channel 30. If the pre-filter channels 70 have changing size and/or dimension, contaminating particles may actually enter the pre-filter channels 70 through the first ends 72 but may then become stuck somewhere along the length of the pre-filter channels 70 due to being too large or having a shape preventing them from flowing further through the pre-filter area or zone 75 towards the second ends 74 of the pre-filter channels 70.

The flow of biological sample continues from the flow input channel 30 through the cell channels 20 and then out into the flow output channel 40 and the third fluid port 41. Any target cells present in the flow of biological sample will be trapped in the cell channels 20 due to the presence of the obstructions 25.

If the pre-filter 50 needs to be cleaned due to contaminating particles clogging the pre-filter channels 70 and/or blocking the entrances of the pre-filter channels 70, a reverse fluid flow can be established from the first fluid port 31 and out through the first filter port 61. The fluid will then flow from the flow input channel 30 and through the pre-filter channels 70 but in the reverse direction, i.e., from the second end 74 towards the first end 72, and then into the filter channel 60. Clogging contaminating particles will then be washed away by the fluid flow and flow out through the first filter port 61. This reverse flow is preferably a flow of a fluid lacking any contaminating particles, such as a culture medium, a wash medium or other liquid.

During the cleaning of the pre-filter 50, by having a flow from the first fluid port 31, the fluid preferably also flows into the cell channels 20, through the flow output channel 40 and out through the third fluid port 41. This flow through the cell channels 20 during the cleaning of the pre-filter 50 reduces the risk of washing away any target cells captured in the cell channels 20. Accordingly, any target cells already captured in cell channels 20 will be retained in the cell channels 20 during the cleaning process.

Figure 6:
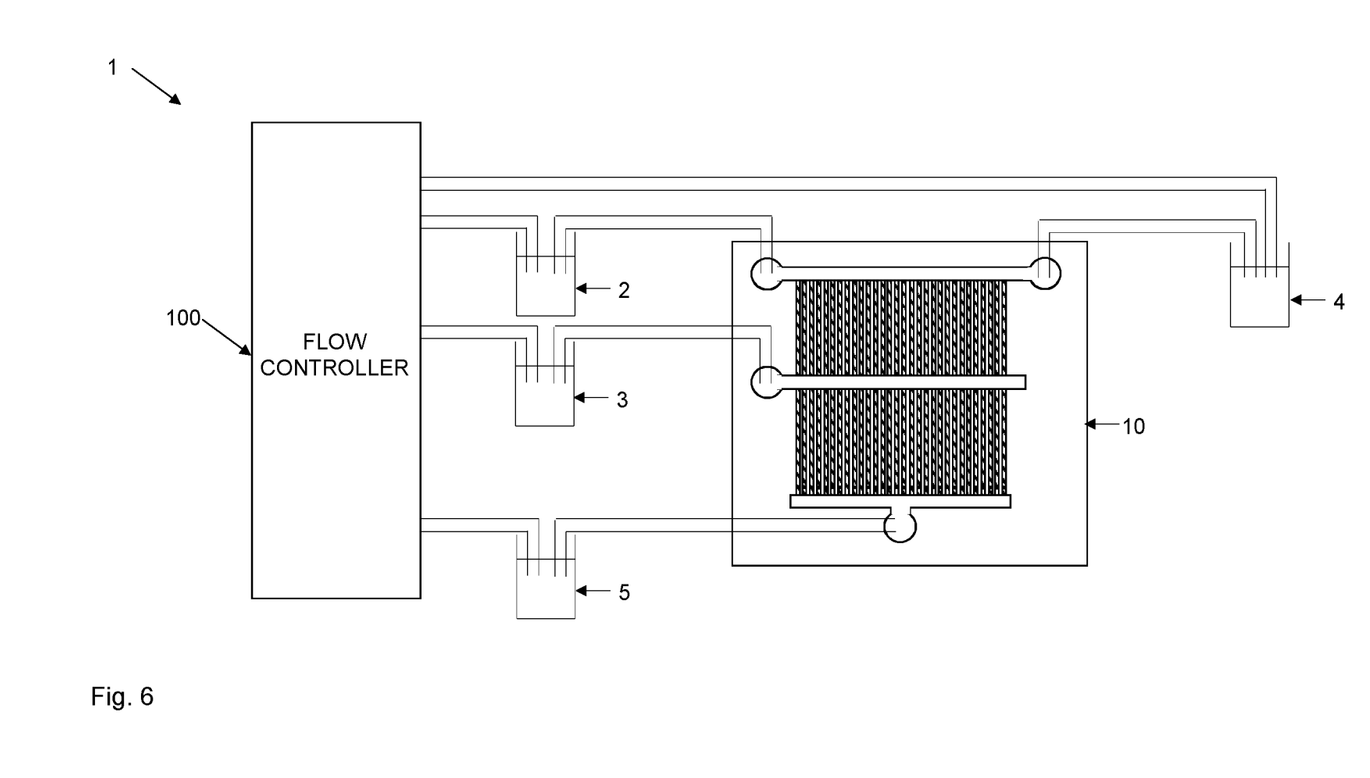
FIG. 6 schematically illustrates a flow controller connected to a microfluidic device according to an embodiment.

In an embodiment, the microfluidic device 1 comprises a flow controller 100, see FIG. 6, configured to induce a fluid flow from the flow input channel 30 through the multiple pre-filter channels 70 and into the filter channel 60.

It is also possible to perform a cleaning of the pre-filter 50 by directing the fluid flow from the third fluid port 41 through the flow output channel 40 and the cell channels 20 and then into the flow input channel 30. The fluid flow then continues through the pre-filter channels 70 and into the filter channel 60 and out through the first filter port 61.

This latter embodiment may be used in particular if no, or very few, target cells have been captured in any of the cell channels 20. If such target cells are present in the cell channels 20 the target cells will, due to the reverse fluid flow, be pushed out from the cell channels 20. Hence, if pre-filter cleaning is to be performed in the microfluidic device 1 with a reverse fluid flow from the third fluid port 41 to the first filter port 61 then an initial verification or check that no captured target cells are present in any cell channel 20 is preferably first conducted. If there are target cells 20 present in cell channels 20, the pre-filter cleaning is preferably instead conducted by directing the reverse flow from the first fluid port 31 to the first filter port 61. As an alternative, it is possible to direct the reverse flow through merely a portion of the cell channels 20, while preventing any reverse flow through selected cell channels 20 comprising target cells. In this approach, a temporary fluid block or restriction is provided at the second end 24 of the selected cell channels 20 comprising target cells thereby preventing the fluid from flowing through these cell channels 20. Such a temporary block or restriction can be achieved, for instance, by providing a pressure on a membrane acting as a lid of the microfluidic device 1 causing a portion of the membrane aligned with the second end 24 of the selected cell channels 20 to depress into and block the second end 24 of the selected cell channels 20. In this further example, a depressable membrane is thereby provided on the substrate 10.

The verification or check of whether there are any target cells in a cell channel 20 and thereby identifying those cell channels 20 that should be temporarily blocked or restricted can be performed according to techniques described further herein.

Figure 2:
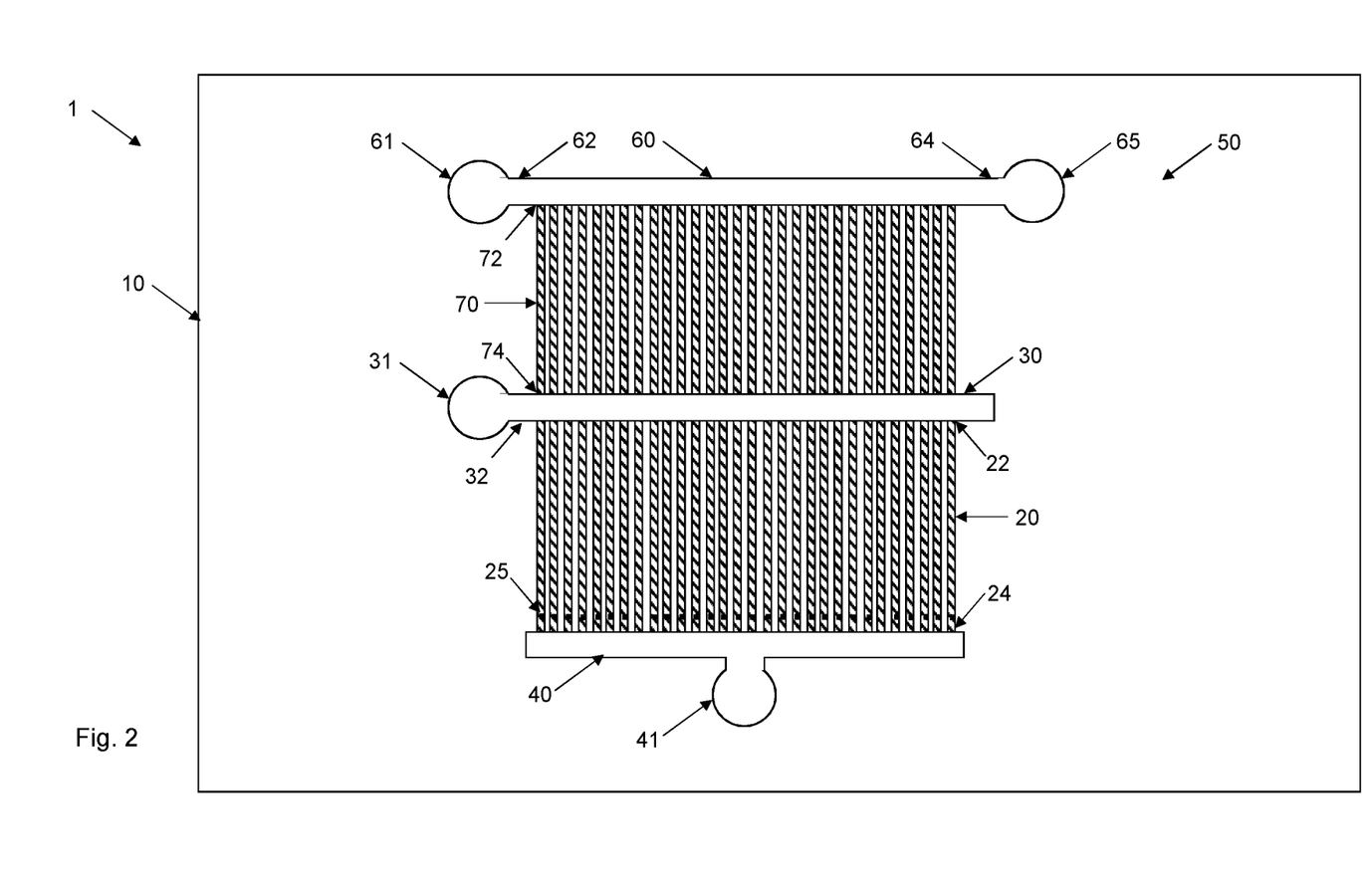
FIG. 2 is an illustration of a microfluidic device according to another embodiment.

FIG. 2 is an illustration of a microfluidic device 1 according to another embodiment. In this embodiment, the microfluidic device 1 comprises a filter channel 60 having a second end 64 in fluid connection with a second filter port 65. Hence, the filter channel 60 has a respective filter port 61, 65 in each of its ends 62, 64.

Having filter ports 61, 65 in both ends 62, 64 of the filter channel 60 enables a prolonged loading and capture phase of the microfluidic device 1, including a continuous culturing of target cells present in the biological sample.

For instance, a flow controller 100, see FIG. 6, could be provided and configured to induce a flow of a fluid comprising the target cells, i.e., the biological sample, back and forth between the first end 62 and the second end 64 of the filter channel 60. This means that the biological sample can flow back and forth between the ends 62, 64, i.e., going from the first end 62 towards the second end 64 and then flowing from the second end 64 back to the first end 62.

In a particular implementation of this embodiment, a first fluid reservoir 2 is connected to the first filter port 61 and a second fluid reservoir 4 is connected to the second filter port 65. In such a case, the flow controller 100 could be configured to induce a flow of the biological sample from the first fluid reservoir 2 through the first filter port 61, through the filter channel 60 and out through the second filter port 65 and into the second fluid reservoir 4. The flow controller 100 is then configured to induce a flow of the biological sample in the opposite direction, i.e., from the second fluid reservoir 4 through the second filter port 65, through the filter channel 60 and out through the first filter port 61 and into the first fluid reservoir 2.

In another embodiment, the flow controller 100 is configured to induce a circular flow of a fluid comprising the target cells, i.e., the biological sample, between the first filter port 61 and the second filter port 65. In this embodiment, the biological sample flows in one and the same direction rather than oscillating back and forth. In such a case, there is a fluid connection between the first filter port 61 and the second filter port 65. This fluid connection preferably comprises at least one fluid reservoir adapted to contain the biological sample. The fluid connection could, for instance, be a tubing or a channel provided in the substrate 10.

In either case, the biological sample can be flown in the filter channel 60 to thereby increase the chances of capturing any target cells present therein in the cell channels 20. In addition, the flowing of the biological sample in the filter channel 60 by the control of the flow controller 100 allows culturing of the target cells in the biological sample. This means that even if the biological sample initially comprises very few target cells, the culturing allows these target cells to grow and multiply during the oscillating or circular flow of the biological sample. Accordingly, the chances of capturing target cells in the cell channels 20 will thereby increase over time.

Figure 3:
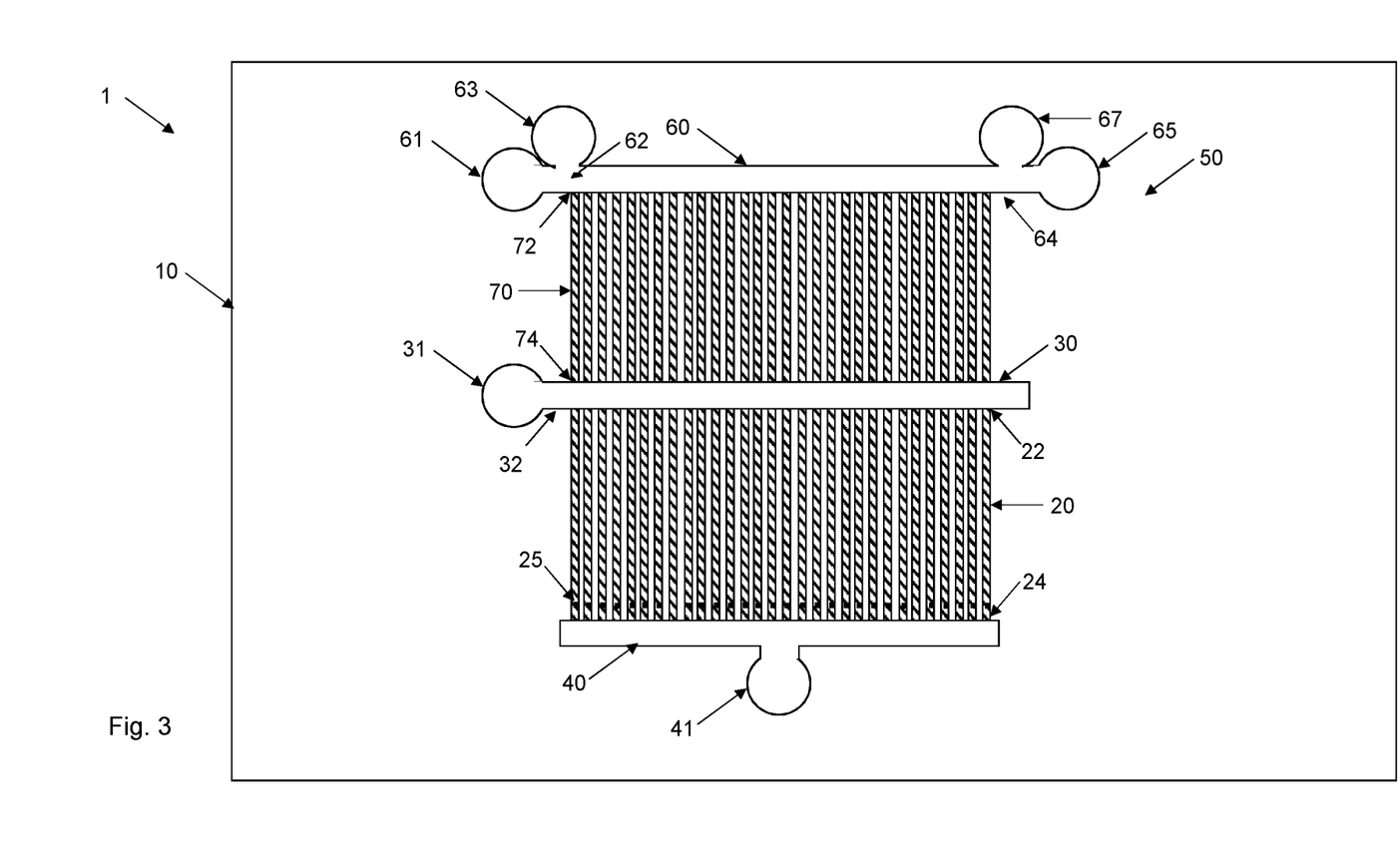
FIG. 3 is an illustration of a microfluidic device according to a further embodiment.

FIG. 3 is an illustration of a further embodiment of the microfluidic device 1. In this embodiment, the filter channel 60 of the microfluidic device 1 has the first end 62 in fluid connection with multiple, i.e., at least two, first filter ports 61, 63 and the second end 64 in fluid connection with multiple second filter ports 65, 67.

This embodiment of the microfluidic device 1 enables mixing the biological sample with a culture medium or other fluid or liquid. For instance, the first and second filter ports 61, 65 could be connected to one or more fluid reservoirs 2, 4 adapted to contain the biological sample as described in the foregoing. In such a case, the first filter port 63 and/or the second filter port 67 could be connected to one or more fluid reservoirs adapted to contain the culture medium or other fluid or liquid. It is also possible to connect one of the first filter port 63 and the second filter port 67 to such a fluid reservoir, while using the other of the first filter port 63 and the second filter port 67 as a waste port.

Figure 4:
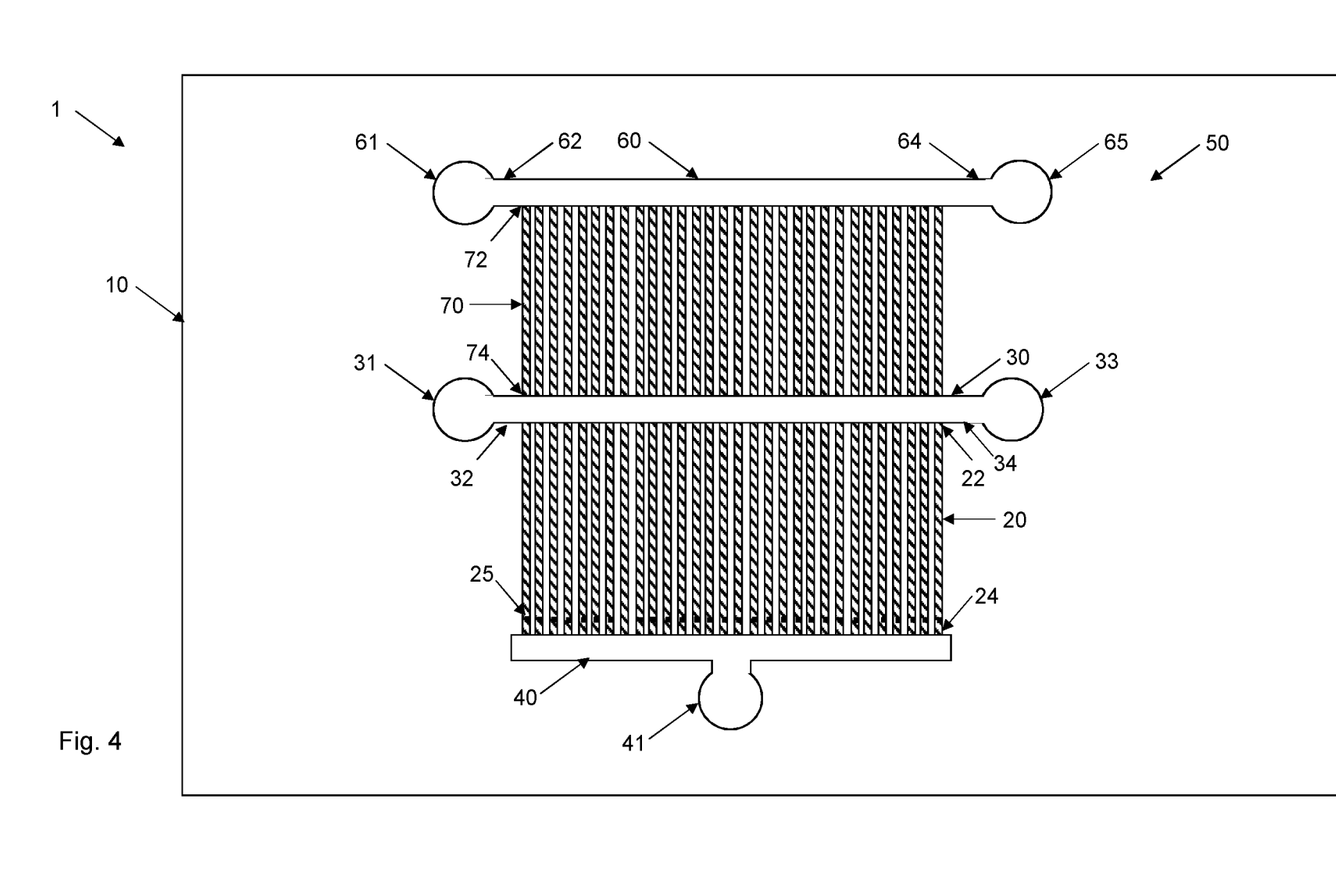
FIG. 4 is an illustration of a microfluidic device according to yet another embodiment.

FIG. 4 is an illustration of a microfluidic device 1 according to yet another embodiment. In this embodiment, the flow input channel 30 of the microfluidic channel 1 has a second end 34 in fluid connection with a second fluid port 33.

Thus, the flow input channel 30 has a respective fluid port 31, 33 connected to each of its respective ends 32, 34. In a further embodiment, at least one of the first end 32 and the second end 34 of the flow input channel 30 could be in fluid connection with multiple fluid ports as was shown in FIG. 3 for the filter channel 60.

Accordingly, embodiments of the microfluidic device 1 include a filter channel 60 having a first end 62 in fluid connection with a first filter port 61 and a flow input channel 30 having a first end 32 in fluid connection with a first fluid port 31; a filter channel 60 having a first end 62 in fluid connection with multiple first filter ports 61, 63 and a flow input channel 30 having a first end 32 in fluid connection with a first fluid port 31; a filter channel 60 having a first end 62 in fluid connection with a first filter port 61 and a flow input channel 30 having a first end 32 in fluid connection with multiple first fluid ports 31; a filter channel 60 having a first end 62 in fluid connection with a first filter port 61 and a second end 64 in fluid connection with a second filter port 65 and a flow input channel 30 having a first end 32 in fluid connection with a first fluid port 31; a filter channel 60 having a first end 62 in fluid connection with multiple first filter ports 61, 63 and a second end 64 in fluid connection with a second filter port 65 and a flow input channel 30 having a first end 32 in fluid connection with a first fluid port 31; a filter channel 60 having a first end 62 in fluid connection with multiple first filter ports 61 and a second end 64 in fluid connection with multiple second filter ports 65, 67 and a flow input channel 30 having a first end 32 in fluid connection with a first fluid port 31; a filter channel 60 having a first end 62 in fluid connection with a first filter port 61 and a flow input channel 30 having a first end 32 in fluid connection with a first fluid port 31 and a second end 34 in fluid connection with a second fluid port 33; a filter channel 60 having a first end 62 in fluid connection with a first filter port 61 and a flow input channel 30 having a first end 32 in fluid connection with multiple first fluid ports 31 and a second end 34 in fluid connection with a second fluid port 33; a filter channel 60 having a first end 62 in fluid connection with multiple first fluid ports 31 and a second end 34 in fluid connection with multiple second fluid ports 33; a filter channel 60 having a first end 62 in fluid connection with a first filter port 61 and a second end 64 in connection with a second filter port 65 and a flow input channel 30 having a first end 32 in fluid connection with a first fluid port 31 and a second end 34 in fluid connection with a second fluid port 33; a filter channel 60 having a first end 62 in fluid connection with a first filter port 61 and a second end 64 in connection with a second filter port 65 and a flow input channel 30 having a first end 32 in fluid connection with multiple first fluid ports 31 and a second end 34 in fluid connection with a second fluid port 33; a filter channel 60 having a first end 62 in fluid connection with a first filter port 61 and a second end 64 in connection with a second filter port 65 and a flow input channel 30 having a first end 32 in fluid connection with multiple first fluid ports 31 and a second end 34 in fluid connection with multiple second fluid ports 33; a filter channel 60 having a first end 62 in fluid connection with multiple first filter ports 61, 63 and a second end 64 in connection with a second filter port 65 and a flow input channel 30 having a first end 32 in fluid connection with a first fluid port 31 and a second end 34 in fluid connection with a second fluid port 33; a filter channel 60 having a first end 62 in fluid connection with multiple first filter ports 61, 63 and a second end 64 in connection with a second filter port 65 and a flow input channel 30 having a first end 32 in fluid connection with multiple first fluid ports 31 and a second end 34 in fluid connection with a second fluid port 33; a filter channel 60 having a first end 62 in fluid connection with multiple first filter ports 61, 63 and a second end 64 in connection with a second filter port 65 and a flow input channel 30 having a first end 32 in fluid connection with multiple first fluid ports 31 and a second end 34 in fluid connection with multiple second fluid ports 33; a filter channel 60 having a first end 62 in fluid connection with multiple first filter ports 61, 63 and a second end 64 in connection with multiple second filter ports 65, 67 and a flow input channel 30 having a first end 32 in fluid connection with a first fluid port 31 and a second end 34 in fluid connection with a second fluid port 33; a filter channel 60 having a first end 62 in fluid connection with multiple first filter ports 61, 63 and a second end 64 in connection with multiple second filter ports 65, 67 and a flow input channel 30 having a first end 32 in fluid connection with multiple first fluid ports 31 and a second end 34 in fluid connection with a second fluid port 33; a filter channel 60 having a first end 62 in fluid connection with multiple first filter ports 61, 63 and a second end 64 in connection with multiple second filter ports 65, 67 and a flow input channel 30 having a first end 32 in fluid connection with multiple first fluid ports 31 and a second end 34 in fluid connection with multiple second fluid ports 33; a filter channel 60 having a first end 62 in fluid connection with multiple first filter ports 61, 63 and a flow input channel 30 having a first end 32 in fluid connection with multiple first fluid ports 31; a filter channel 60 having a first end 62 in fluid connection with multiple first filter ports 61, 63 and a flow input channel 30 having a first end 32 in fluid connection with a first fluid port 31 and a second end 34 in fluid connection with a second fluid port 33; a filter channel 60 having a first end 62 in fluid connection with multiple first filter ports 61, 63 and a flow input channel 30 having a first end 32 in fluid connection with multiple first fluid ports 31 and a second end 34 in fluid connection with a second fluid port 33; a filter channel 60 having a first end 62 in fluid connection with multiple first filter ports 61, 63 and a flow input channel 30 having a first end 32 in fluid connection with multiple first fluid ports 31 and a second end 34 in fluid connection with multiple second fluid ports 33; a filter channel 60 having a first end 62 in fluid connection with a first filter port 61 and a second end 64 in fluid connection with a second filter port 65 and a flow input channel 30 having a first end 32 in fluid connection with multiple first fluid ports 31; a filter channel 60 having a first end 62 in fluid connection with multiple first filter ports 61, 63 and a second end 64 in fluid connection with a second filter port 65 and a flow input channel 30 having a first end 32 in fluid connection with multiple first fluid ports 31; a filter channel 60 having a first end 62 in fluid connection with multiple first filter ports 61, 63 and a second end 64 in fluid connection with multiple second filter ports 65, 67 and a flow input channel 30 having a first end 32 in fluid connection with multiple first fluid ports 31.

The concept of having one or multiple fluid ports can also be applied to the flow output channel 40, which could comprise a single fluid port 41, a respective fluid port in fluid connection with a respective end of the flow output channel 40, multiple fluid ports in fluid connection with a first end of the flow output channel 40 and a fluid port in fluid connection with a second end of the flow output channel 40 or multiple fluid ports in fluid connection with the first end and multiple fluid ports in fluid connection with the second end.

Figure 5:
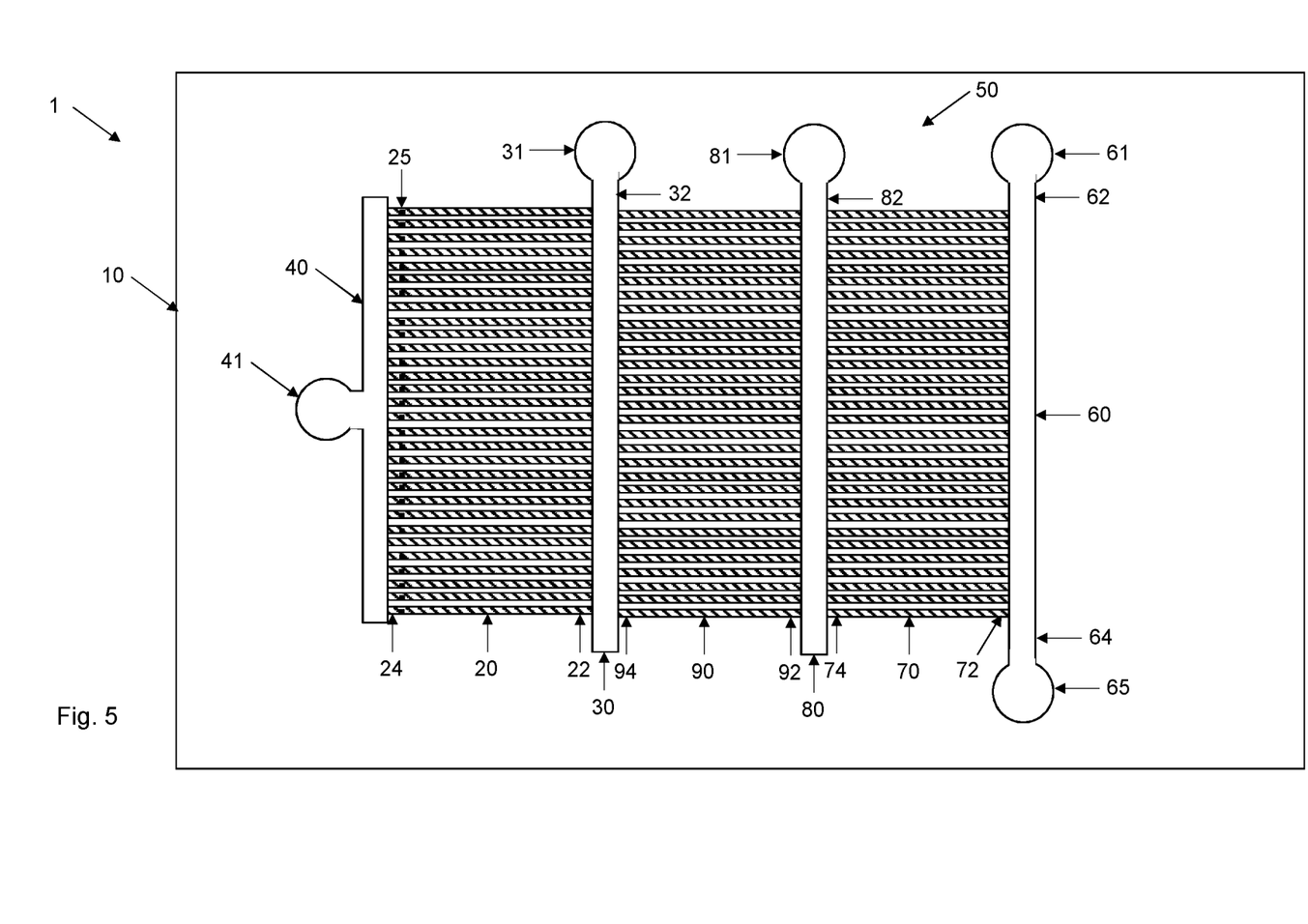
FIG. 5 is an illustration of a microfluidic device according to a further embodiment.

FIG. 5 is an illustration of yet another embodiment of a microfluidic device 1 having multiple sets of pre-filter channels 70, 90. In this embodiment, the filter channel 60 is a first filter channel 60 and the pre-filter channels 70 are first pre-filter channels 70. The pre-filter 50 also comprises a second filter channel 80 having a first end 82 in fluid connection with a third filter port 81 and second pre-filter channels 90 adapted to accommodate the target cells. A respective first end 92 of the second pre-filter channels 90 is in fluid connection with the second filter channel 80 and a respective second end 94 of the second pre-filter channels 90 is in fluid connection with the flow input channel 30. In this embodiment, the respective second end 74 of the first pre-filter channels 70 is in fluid connection with the second filter channel 80.

Thus, the embodiment as illustrated in FIG. 5 comprises a pre-filter 50 with multiple, i.e., at least two, sets of filter channels 60, 80 and pre-filter channels 70, 90. These sets are then arranged in series in the substrate 10 with an upstream set of the first filter channel 60 and the first pre-filter channels 70 and a downstream set of the second filter channel 80 and the second pre-filter channels 90 and where upstream vs. downstream relates to a flow direction from the first filter channel 60 towards the flow output channel 40.

In an embodiment, the second pre-filter channels 90 and the first pre-filter channels 70 have the same diameter, width and height and the same cross-sectional shape. This means that the two sets of filter channels 60, 80 and pre-filter channels 70, 90 are substantially the same. In another embodiment, the second pre-filter channels 90 may have a different diameter, width and height and/or cross-sectional shape as compared to the first pre-filter channels 70. In particular, the first pre-filter channels 70 have a larger diameter or a larger height and/or width as compared to the second pre-filter channels 90.

Accordingly, the cross-sectional area of the pre-filter channels 70, 90 is preferable larger for the first pre-filter channels 70 as compared to the second pre-filter channels 90. If at least one of the first and second pre-filter channels 70, 90 have narrowing cross-sectional shape then the diameter, width and/or height of the first pre-filter channels 70 at the second end 74 is preferably larger than the diameter, width and/or height of the second pre-filter channels 90 at the second end 94.

Both the first and second pre-filter channels 70, 90 could have uniform cross-sectional shape and size when traveling from the first end 72, 92 to the second end 74, 94. Alternatively, one or both of the first and second pre-filter channels 70, 90 could have different cross-sectional shape and size at the first end 72, 92 as compared to the second end 74, 94, such as continuously or step-wise narrowing pre-filter channels 70, 90.

This concept of having multiple filter channels 60, 80 and multiple pre-filter channels 70, 90 can of course be extended to more than two sets of such filter channels 60, 80 and pre-filter channels 70, 90, possibly with different dimensions.

The first filter channel 60 and the second filter channel 80 could have any number of filter ports as described in the foregoing and as exemplified in FIGS. 1-3.

The pre-filter 50 shown in FIG. 5 can be cleaned from clogging contaminating particles according to various embodiments. For instance, each set of pre-filter channels 70, 90 can be individually cleaned. A separate cleaning of the first pre-filter channels 70 can be performed by directing a reverse flow from the third filter port 81 through the second filter channel 80 and the first pre-filter channels 70 and the first filter channel 60 and out though the one of its connected filter ports 61, 65. Correspondingly, a separate cleaning of the second pre-filter channels 90 may be performed by directing a reverse flow from the first fluid port 31 through the flow input channel 30 and the second pre-filter channels 90 and the second filter channel 80 and out through the third filter port 81.

Alternatively, the two sets of pre-filter channels 70, 90 can be cleaned in a combined operation by providing a reverse flow from the first fluid port 31, the flow input channel 30 and through the second pre-filter channels 90, the second filter channel 80, the first pre-filter channels 70 and the first filter channel 60 and out through any or all of its connected filter ports 61, 63. This combined cleaning may alternatively also include a reverse flow through all or a selected portion of cell channels 20 as previously described herein by providing the fluid flow from the third fluid port 41.

The flow controller 100 can be implemented according to various embodiments in order to direct and control the flows of fluid, such as the biological sample and optional culture medium or other fluid or liquid, through the microfluidic device 1.

FIG. 6 illustrates an embodiment in which each filter and fluid port is connected to a respective fluid reservoir 2, 3, 4, 5, which in turn are connected to and controlled by the flow controller 100. This means that the flow controller 100 will control the flow of fluid from or towards the respective fluid reservoirs 2, 3, 4, 5 depending on what operation to perform, such as loading of the microfluidic device 1 with a biological sample, capture of target cells in the cell channels 20, cleaning of pre-filter 50, culturing target cells in cell channels 20 or culturing target cells in an oscillating or circulation flow, etc.

In an embodiment, the flow controller 100 is a pressure controller providing a pressure-driven flow. In such a case, the pressure controller is configured to control a fluid pressure applied to the filter ports 61, 65, 81 and fluid ports 31, 41 to control the direction of the fluid flow. For instance, in order to achieve an oscillating flow of the biological sample in the first filter channel 60, the pressure controller is preferably configured to control a fluid pressure applied to the first filter port 61 and the second filter port 65 to induce a flow of a fluid comprising the target cells back and forth between the first end 62 and the second end 64 of the first filter channel 60.

A non-limiting, but illustrative, example of such a pressure controller that can be used is proportional pressure regulator VEAB by Festo AG.

Other flow control solutions could include using one or more pumps in connection with valves in order to control the direction of fluid flow.

In FIGS. 1 to 6, the pre-filter 50 has been illustrated as being arranged or provided in the same substrate 10 as the cell channels 20, the flow input channel 30 and the flow output channel 40. Such an implementation is possible. In an alternative embodiment, the pre-filter 50 is arranged or provided in a first substrate, whereas the cell channels 20, the flow input channel 30 and the flow output channel 40 are arranged or provided in a second substrate 10 of the microfluidic device 1. Both embodiments are possible as long as the pre-filter 50 is in fluid connection with the flow input channel 30.

The substrate 10, or the substrates, of the microfluidic device 1 may be made of any material, such as plastic material, in which the structures constituting the cell channels 20, the flow input channel 30, the flow output channel 40 and the pre-filter 50 can be defined. The fluid ports 31, 33, 41 and filter ports 61, 63, 65, 67, 81 can be present in the substrate 10. Alternatively, they may be provided outside of the substrate 10 and are then preferably connected to the respective ends 32, 34, 62, 64, 82 of the flow input channel 30, flow output channel 40 and filter channels 60, 80 with a respective tubing.

Non-limiting examples of suitable materials for the substrate 10 include ZEONEX® and ZEONOR®, which are cyclic olefin polymers (COP) marketed by ZEON Chemicals L.P. and TOPAS®, which are cyclic olefin copolymers (COC) marketed by Topas Advanced Polymers. These materials have excellent optical characteristics in terms of transmission and background fluorescence. They also have good flow characteristics when heated and may therefore replicate small structures allowing formation of substrates of the microfluidic device.

Other examples of suitable materials for the substrate 10 include glasses, polydimethylsiloxane (PDMS), poly(methyl methacrylate) (PMMA), polycarbonate (PC), polypropylene (PP), polytetrafluoroethylene (PTFE), polyethylene terephthalate (PET) and poly(p-phenylene sulfide) (PPS).

The substrate 10 is preferably transparent to allow imaging through the substrate 10.

In an embodiment, a lid (not illustrated) is arranged onto the substrate 10. This lid then functions as a cover or lid for the channels 20, 30, 40, 60, 70, 80, 90 defined in the substrate 10. The lid could be made of a plastic material or glass. The lid is preferably transparent to allow imaging through the lid.

The microfluidic device 1 of the present embodiments is useful for monitoring or analyzing phenotypic characteristics of target cells present in a biological sample.

In an embodiment, the biological sample is a blood sample, such as a whole blood sample, a diluted blood sample or a blood culture sample. Other examples of biological samples include other body fluid samples, such as a urine sample, a saliva sample, a feces sample, a cerebrospinal fluid sample, an amniotic fluid sample, a milk sample, a sputum derived sample or a lymph sample. Alternatively, the biological sample could be obtained from a body tissue, such as a biopsy. Other examples include food sample tested for bacterial contaminations, milk from cow, goats or other milk producing animals for mastitis testing, etc. Actually, any biological sample that comprises cells and that can be loaded into a microfluidic device 1 can be used according to the embodiments.

In an embodiment, the phenotypic characterization of the target cells in the cell channels 20 is performed by determining a phenotypic response of the target cells to a test agent. Hence, in such an approach the target cells in the cell channels 20 are exposed to a test agent. This test agent could be any molecule, compound, composition, or a mixture of molecules, compounds or compositions. In related embodiments, the target cells are more generally exposed to one or more stimuli in the cell channels 20. Such one or more stimuli do not necessarily have to be a test agent but could instead be a change in environmental conditions, such as temperature change. Thus, the phenotype response of the target cells to the one or more stimuli is then determined.

Hence, in an embodiment the target cells in the cell channels 20 are exposed to a test agent. This test agent could be included in the biological sample itself. Alternatively, the test agent could be added, such as in a culture medium or other fluid or liquid, using one of the ports of the microfluidic device 1, typically one of the first fluid port 31 and the second fluid port 33.

Determining the phenotypic response of the target cells to the test agent could include determining at least one of growth rate, shape, size, form of growth rate curve defining growth rate over time, form of length curve defining cell length over time, form of area curve defining cell area over time, color, optical density, absorption spectra, conductivity, heat production or a mixture thereof for the target cells.

The determination of the phenotypic response of the target cells typically involve monitoring the target cells in the cell channels 20 at one or multiple time instances. Thus, depending on the particular phenotypic response of the target cells to the test agent it might be sufficient to monitor the target cells once or at multiple time instances.

The monitoring of the target cells could include taking at least one image of the target cells in the cell channels 20. A single image at a single time instance could be taken or multiple images at multiple time instances are taken.

In a particular embodiment, the at least one image is taken using a microscopy, such as a phase contrast microscope, connected to a camera, such as a charge-coupled device (CCD) camera or a complementary metal-oxide semiconductor (CMOS) camera, or a confocal scanning system for fluorescence, Raman imaging, Coherent Anti-stokes Raman Scattering (CARS), Stimulated Raman Scattering (SRS) and similar chemically sensitive techniques that gives spectral changes for dead and live cells. This includes measurements in one or several wavelengths with or without contrast enhancing additions to the growth media, such as chemically specific probes and dyes.

An image is not necessarily a 2D photo of an area but can also correspond to, for example, line scans in selected positions in the microfluidic device 1.

Other techniques of detecting presence of target cells in cell channels 20 could be used instead of or as a complement to taking images of the cell channels 20, such as measuring conductivity through the cell channels 20 or the heat production in the cell channels 20 using electronic measurement equipment.

In a first implementation example, the test agent is an antibiotic. In this implementation example, the microfluidic device 1 can be used to determine a susceptibility of target cells, such as bacteria, to the antibiotic.

In a second implementation example, the test agent is a cytostatic. In such an implementation example, the microfluidic device 1 is used to determine a susceptibility of the target cells, such as cancer cells, to the cytostatic based on the monitoring of target cells in the cell channels 20.

In a third implementation example, the test agent is a probe, such as a fluorescent in situ hybridization (FISH) probe. In such a case, the FISH probe can be used to identify the particular target cells captured in the cell channels 20 based on the monitoring of the target cells in the cell channels 20. Different such FISH probes target different target cells, thereby enabling determination of the identity of the target cells depending on whether the FISH probe binds specifically to the target cell or not. The FISH probes can target species-specific RNA or DNA sequences, such as 23S rRNA. For more information of using FISH probes for identifying microorganisms in blood culture reference is made to Kempf et al., *Journal of Clinical Microbiology*

2000, 38(2): 830-838. FISH probes adapted for different bacteria can be found on http://probebase.csb.univie.ac.at/node/8.

The identification of species can advantageously be combined with determining the phenotypic response of the target cells against a test agent according to any of the above presented implementation examples. In such a case, the species identification is preferably done after the phenotypic response to antibiotics or cytostatics. In this way, the species identification may facilitate the interpretation of the phenotypic response to the test agent in the cell channels 20, which is particularly advantageous if the biological sample comprises a mixture of target cells of species or strains.

Figure 9:
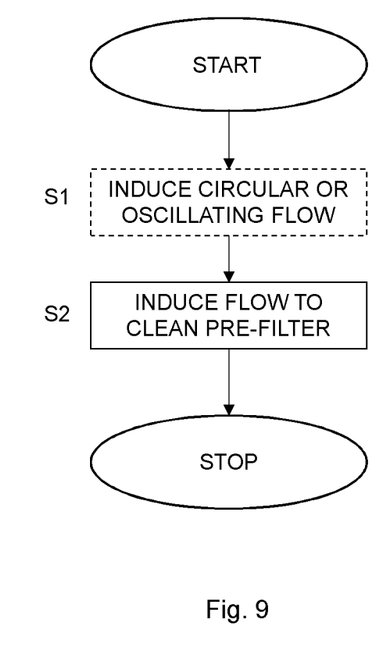
FIG. 9 is flow chart illustrating an embodiment of operating a microfluidic device according to an embodiment.

FIG. 9 is a flow chart illustrating a method of operating a microfluidic device 1 according to the present embodiments. The method comprises inducing, in step S2, a fluid flow from the flow input channel 30 through the pre-filter channels 70 and into the filter channel 60.

Hence, this method of operating the microfluidic device 1 as defined in step S2 relates to cleaning the pre-filter 50 of the microfluidic device 1 from clogging contaminating particles.

In an embodiment, the fluid flow is also induced in step S2 to flow from the flow input channel 30 through the cell channels 20 and into the output channel 40. In this way it is possible to reverse the flow and clean the pre-filter 50 while maintaining the flow direction through the cell channels 20.

In a particular embodiment, step S2 comprises applying a fluid pressure to the first fluid port 31 to induce a fluid flow from the flow input channel 30 through the pre-filter channels 70 and into the filter channel 60.

In an embodiment, step S2 comprises inducing a fluid flow from the flow output channel 40 through at least a portion of the cells channels 20 into the flow input channel 30 through the pre-filter channels 70 and into the filter channel 70.

In this embodiment, the cleaning operation involves providing a reverse flow that also passes through at least a selected portion of the cell channels 20. As has been described in the foregoing, the selected portion of the cell channels 20 preferably lacks any captured target cells. Hence, the reverse flow is preferably prevented or at least significantly reduced from flowing through any cell channels 20 that comprise target cells to thereby reduce the risk of washing away previously captured target cells.

The identification of the cell channels 20 that comprise target cells can be performed based on taking one or more images of the cell channels 20 as described in the foregoing.

In an embodiment, fluorescent probes specifically binding to a marker may be used to mark and tag target cells. In such a case, target cells present in cell channels 20 can be identified by measuring fluorescence in the cell channels 20. The fluorescent probe binds specifically to a marker. This marker can be a molecule, such as a protein, in the target cells or in the cell membrane of the target cells, such as a receptor. Alternatively, the marker could be a nucleic acid molecule, such as a particular DNA or gene sequence or a particular mRNA sequence.

The fluorescent probe can, for instance, be an intercalating DNA binding dye that clearly distinguishes target cells from contaminating particles. The fluorescent probe can be a life-death screening dye, which only enters dead cells.

The fluorescent probe can be a fluorescent antibody that binds specifically to the target cells, which enables differentiation of for example, different bacterial species with different surface antigens, cancer cells from other cells based on surface antigens, circulating fetal cells from the pregnant woman's own cells.

The fluorescent probe can be a fluorescent oligonucleotide that targets a species specific RNA, such as the 16S or 23S ribosomal RNA.

Specifically binding of a fluorescent probe can be determined based on affinity and/or avidity. The affinity, represented by the equilibrium constant for the dissociation of the target marker with the fluorescent probe ($K_d$), is a measure for the binding strength between the target maker and the fluorescent probe. The lesser the value of $K_d$, the stronger the binding strength. Alternatively, the affinity can also be expressed as the affinity constant ($K_a$), which is $1/K_d$. As will be clear to the skilled person, affinity can be determined in a manner known per se, depending on the specific target marker of interest.

Avidity is the measure of the strength of binding between a fluorescent probe and the target marker. Avidity is related to both the affinity between the target marker and the binding site on the fluorescent probe and the number of binding sites present on the fluorescent probe.

Generally, any $K_d$ value greater than $10^{-4}$ M (or any $K_a$ value lower than $10^4 \, M^{-1}$) is generally considered to indicate non-specific binding.

Specific binding of a fluorescent probe to a target maker can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

In the foregoing, the probe has been exemplified by a fluorescent probe. The embodiments are, however, not limited thereto. Actually any probe that can be detectable and measured could be used according to the embodiments, such as fluorescent probes, dyed probes, chemiluminescent probes, radiolabeled probes, gold beads, etc.

The method may also comprise the optional step S1. In such a case, the filter channel 60 of the microfluidic device 1 has a second end 64 in fluid connection with a second fluid port 65. In an embodiment, this step S1 comprises inducing a flow of a fluid comprising the target cells back and forth between the first end 62 and the second end 64 of the filter channel 60.

For instance, this step S1 can be obtained by controlling a fluid pressure applied to the first filter port 61 and the second filter port 65 to induce a flow of the fluid comprising the target cells back and forth between the first end 62 and the second end 64 of the filter channel 60.

In another embodiment, step S1 comprises inducing a circular flow of a fluid comprising the target cells between the first filter port 61 and the second filter port 65.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:
1. A microfluidic device comprising:
a first fluid port;
a third fluid port;

a substrate having cell channels adapted to accommodate target cells;
a flow input channel having a first end in fluid connection with said first fluid port, wherein a respective first end of said cell channels is in fluid connection with said flow input channel; and
a flow output channel in fluid connection with said third fluid port, wherein a respective second end of said cell channels is in fluid connection with said flow output channel, wherein said cell channels comprise a respective obstruction designed to prevent said target cells from passing said respective obstruction and into said flow output channel and to capture said target cells in said cell channels;
a pre-filter comprising:
a first filter port;
a filter channel having a first end in fluid connection with said first filter port; and
pre-filter channels adapted to accommodate said target cells and capture contaminating particles, wherein a respective first end of said pre-filter channels is in fluid connection with said filter channel and a respective second end of said pre-filter channels is in fluid connection with said flow input channel; and
a flow controller in fluidic connection with the first and third fluid ports and/or the first filter port, wherein the flow controller is configured to induce a fluid flow from said flow input channel through said pre-filter channels and into said filter channel to clean contaminating particles clogging said pre-filter channels and/or blocking entrances of said pre-filter channels.

2. The microfluidic device according to claim 1, wherein said pre-filter comprises a second filter port and said filter channel has a second end in fluid connection with said second filter port.

3. The microfluidic device according to claim 2, wherein said flow controller is further configured to induce a flow of a fluid comprising said target cells back and forth between said first end and said second end of said filter channel.

4. The microfluidic device according to claim 2, wherein said flow controller is further configured to induce a circular flow of a fluid comprising said target cells between said first filter port and said second filter port.

5. The microfluidic device according to claim 1, wherein said flow controller is configured to induce said fluid flow from said flow input channel through said pre-filter channels and into said filter channel and from said flow input channel through said cell channels and into said flow output channel.

6. The microfluidic device according to claim 1, wherein said filter channel is a first filter channel;
said pre-filter channels are first pre-filter channels;
said pre-filter comprises:
a third filter port;
a second filter channel having a first end in fluid connection with said third filter port; and
second pre-filter channels adapted to accommodate said target cells and capture said contaminating particles, wherein a respective first end of said second pre-filter channels is in fluid connection with said second filter channel and a respective second end of said second pre-filter channels is in fluid connection with said flow input channel;
said respective second end of said first pre-filter channels is in fluid connection with said second filter channel.

7. The microfluidic device according to claim 6, wherein said first pre-filter channels have a larger diameter or a larger height and/or width as compared to said second pre-filter channels.

8. A method of operating a microfluidic device according to claim 1, said method comprising inducing a fluid flow from said flow input channel through said pre-filter channels and into said filter channel to clean contaminating particles clogging said pre-filter channels and/or blocking entrances of said pre-filter channels from said pre-filter.

9. The method according to claim 8, wherein inducing said fluid flow comprises inducing a fluid flow from said flow input channel through said pre-filter channels and into said filter channel and from said flow input channel through said cell channels and into said flow output channel.

10. The method according to claim 8, wherein inducing said fluid flow comprises inducing a fluid flow from said flow output channel through at least a portion of said cell channels into said flow input channel through said pre-filter channels and into said filter channel.

11. The method according to claim 8, wherein
said pre-filter comprises a second filter port;
said filter channel has a second end in fluid connection with said second filter port; and
said method further comprises inducing a flow of a fluid comprising said target cells back and forth between said first end and said second end of said filter channel.

12. The method according to claim 8, wherein
said pre-filter comprises a second filter port;
said filter channel has a second end in fluid connection with said second filter port; and
said method further comprises inducing a circular flow of a fluid comprising said target cells between said first filter port and said second filter port.

* * * * *